United States Patent [19]

Kennedy et al.

[11] 3,954,660

[45] May 4, 1976

[54] ANIONIC SURFACTANT SLURRY HAVING INCREASED VISCOSITY AND METHOD OF PROVIDING SAID SLURRY

[75] Inventors: E. Flynt Kennedy; Dean R. Weimer, both of Ponca City, Okla.

[73] Assignee: Continental Oil Company, Ponca City, Okla.

[22] Filed: July 23, 1974

[21] Appl. No.: 491,016

[52] U.S. Cl. .............................. 252/353; 252/170; 252/173; 252/550
[51] Int. Cl.² ................... B01F 17/02; B01F 17/12; C11D 3/20
[58] Field of Search ............. 252/353, 355, DIG. 13, 252/173, 170, 550

[56] References Cited
UNITED STATES PATENTS

| | | |
|---|---|---|
| 2,189,803 | 12/1937 | Katzman et al. ................. 252/355 X |
| 2,307,047 | 5/1941 | Katzman et al. ................. 252/355 X |
| 3,794,601 | 2/1974 | Kennedy ......................... 252/353 X |

*Primary Examiner*—Benjamin R. Padgett
*Assistant Examiner*—David Leland
*Attorney, Agent, or Firm*—F. Lindsey Scott

[57] ABSTRACT

The viscosity of anionic surfactant slurries is increased by admixing with such slurries an effective amount of a viscosity increasing additive selected from the group consisting of dialkyl ethers wherein the alkyl radicals of said ethers contain from 2 to 5 carbon atoms, alkoxyethoxyethanols wherein the alkyl radical contains from 2 to 6 carbon atoms, and tertiary amines wherein the alkyl radical contains from 2 to 4 carbon atoms.

12 Claims, No Drawings

3,954,660

ANIONIC SURFACTANT SLURRY HAVING INCREASED VISCOSITY AND METHOD OF PROVIDING SAID SLURRY

FIELD OF THE INVENTION

This invention relates to anionic surfactant slurries having increased viscosities. In one aspect, this invention relates to a method for increasing the viscosity of an anionic surfactant slurry by the addition of a viscosity increasing additive selected from the group consisting of dialkyl ethers, wherein the alkyl radicals contain from about 2 to 5 carbon atoms, alkoxyethoxyethanols wherein the alkyl radical contains from 2 to 6 carbon atoms, and tertiary amines wherein the alkyl radicals contain from 2 to 4 carbon atoms.

PRIOR ART

Anionic surfactant materials have been prepared by a variety of processes such as sulfation and sulfonation with gaseous $SO_3$, chlorosulfonic acid and the like. In most such processes an anionic surfactant slurry results. Such slurries typically contain the anionic surfactant material, free oil, water and inorganic salts. To facilitate further processing, it is desirable that the viscosity of such slurries be increased so that such slurries possess improved foam stability and, at the same time, enhance the aesthetic value of the product produced from such slurries. Most prior art methods for increasing the viscosity of such slurries have involved the addition of viscosity increasing additives which have the disadvantage that the solubility characteristics of the product are often modified by the addition of such additives. Further, the addition of such viscosity increasing additives often results in a breakdown of the formulation, thus detracting from the desire of the consumer to use such products. Accordingly, much time and effort has been devoted to a search for a method for increasing the viscosity of such slurries which does not suffer the same disadvantages.

OBJECTS OF THE INVENTION

It is an object of this invention to provide a method for increasing the viscosity of an anionic surfactant slurry.

Another object of the invention is to provide a method for increasing the viscosity of alcohol sulfate containing slurries.

It is a further objective of this invention to provide anionic surfactant slurries having improved viscosity.

SUMMARY OF THE INVENTION

It has been found that the objectives of the present invention are achieved by admixing with anionic surfactant slurries an effective amount of a viscosity increasing additive selected from the group consisting of dialkyl ethers having the general formula R-O-R' wherein R and R' are alkyl groups containing from 2 to 5 carbon atoms, alkoxyethoxyethanols having the general formula R''-O (CH$_2$CH$_2$O)$_x$H, wherein x varies from about 1 to 2 and R'' is an alkyl group containing from 2 to 6 carbon atoms, and tertiary amines having the general formula R'''$_3$N, wherein R''' is an alkyl group containing from 2 to 4 carbon atoms.

DESCRIPTION OF THE PREFERRED EMBODIMENTS

The method of the present invention is useful for increasing the viscosity of anionic surfactant slurries. The method is particularly useful for increasing the viscosity of alcohol sulfate containing surfactant slurries. Such slurries typically contain the anionic surfactant materials, free oil remaining from the surfactant forming reaction, water, inorganic salts, and the like. While the slurry composition may vary widely, a typical slurry would contain from about 25 to about 60 weight percent anionic surfactant material, from about 0.5 to 5 weight percent free oil, up to about 1.0 weight percent inorganic salt with the balance being water (i.e., up to about 75 weight percent water).

Such slurries are useful as surfactants and raw materials in the production of anionic surfactant containing products. Slurries are particularly useful as raw materials in that the slurries are readily shipped as anionic surfactant intermediates for formulation at remote locations into a variety of anionic surfactant products. As previously stated, the anionic surfactant slurry having an increased viscosity, and the method for producing same, of the present invention is especially useful in the production of light duty liquid dishwashing detergents or shampoos, especially those containing alcohol sulfate as the anionic surfactant material. Especially desirable results are obtained when the anionic surfactant material is an alcohol sulfate containing from about 10 to about 16 carbon atoms. However, it is to be understood that other anionic surfactant materials such as ether sulfates containing from about 10 to about 16 carbon atoms and from 0.5 to 5 moles of ethylene oxide per mole of alcohol, alkyl benzene sulfonates containing from about 10 to about 14 carbon atoms in the alkyl portion, alkyl hydroxy sulfonates containing from about 10 to about 20 carbon atoms, alkene sulfonates containing from about 12 to about 20 carbon atoms, mixtures thereof and the like are suitable.

Some specific examples of such anionic surfactants are dodecyl alcohol sulfate, hexadecyl alcohol sulfate, dodecyl ethoxy sulfate, tetradecyl ethoxy sulfate, decylbenzene sulfonate, tetradecyl benzene sulfonate, tetradecyl sulfonate, octadecyl sulfonate, 3-hydroxy-1-hexadecane sulfonate, 2-hexadecene 1-sulfonate and the like. Such compounds are generally referred in the art by the type material, i.e., alcohol sulfates, ethoxylated alcohol sulfates, etc, and the number of carbon atoms in the hydrocarbon portion. Such terminology will be used hereinafter.

As previously stated, the majority of the material present in the slurry, with the exception of water, is the anionic surfactant material. However, the slurry will, in addition to water and the anionic material, contain a small but significant amount of free oil and inorganic salt.

The free oil is normally unreacted charge material, organic by-products of the reaction and the like. The inorganic salt present in the slurry results from the reaction of the residual sulfating or sulfonating acids with the cations used to neutralize the organic sulfuric and sulfonic acids corresponding to the anionic sulfate and sulfonate materials. Suitable cations for neutralizing the acids are sodium, potassium, calcium, and magnesium. The cation may be added in any suitable forms such as the hydroxide of the cations listed above. Particularly desirable results have been achieved wherein the salt was selected from the group consisting of sodium hydroxide, potassium hydroxide, and magnesium hydroxide.

The acids may be neutralized with ammonia or substituted amines such as diethanol amines, diethyl amine, and the like. Particularly desirable results have been achieved wherein ammonia was used to neutralize the acids.

The viscosity of the anionic surfactant slurries such as described above may be increased substantially by admixing with such slurries an effective amount of a viscosity increasing additive selected from the group consisting of dialkyl ethers having a general formula R-O-R', wherein R and R' are alkyl groups, each containing from about 2 to 5 carbon atoms with R plus R' containing from about 4 to 10 carbon atoms, alkoxyethoxyethanols having the general formula R''-O-$(CH_2CH_2O)_xH$, wherein $x$ varies from about 1 to 2 and R'' is an alkyl containing from 2 to 6 carbon atoms, tertiary amines having the general formula R'''$_3$N, wherein R''' is an alkyl group containing from 2 to 4 carbon atoms, and the total number of carbons in said tertiary amines is from about 6 to 12 carbon atoms and mixtures thereof. When the viscosity increasing additive is a dialkyl ether, as described above, care must be exercised that the alkyl portions of said ether do not contain more than 5 carbon atoms if one is to obtain the desired results of increasing the viscosity of anionic surfactant slurries.

Examples of suitable dialkyl ethers which can be employed as the viscosity increasing additive in the practice of the present invention are diethyl ether, dibutyl ether, and dipentyl ether and mixtures thereof. Examples of suitable alkoxyethoxyethanols are 2-alkoxyethanol, 2-hexoxyethanol, and diethylene glycol monohexylether. Illustrative of the tertiary amines, as previously defined, which can be employed in the practice of the present invention are triethylamine and tributylamine.

The amount of the viscosity increasing additive employed in practicing the present invention can vary widely, but will generally be from about 0.5 to 6 weight percent based on the total weight of the slurry. Particularly desirable results have been obtained wherein the viscosity increasing additive is present in an amount equal to about 1 weight percent of the slurry.

The viscosity increasing additive may be added by any convenient method and is effective in increasing the viscosity of anionic surfactant materials when such additive is intimately mixed with the surfactant slurry. Thus, any suitable means of introducing the viscosity increasing additive can be employed, the only requirement being that for the most desirable results, the method employed must insure that such addition is effectively and completely mixed with the surfactant.

In order to more fully describe the present invention, the following example is set forth. However, it is to be understood that many variations and modifications in the procedures set forth therein, including slurry proportions and the like are possible, and that such modifications and variations are within the scope of the present invention.

EXAMPLE

An alcohol sulfate slurry was prepared containing 33.45 weight percent alcohol sulfate, wherein said alcohol sulfate was produced from a mixture of alcohols containing about 67 weight percent n-$C_{12}$, about 27 weight percent n-$C_{14}$ alcohol and about 6 weight percent n-$C_{16}$ alcohol; 0.86 weight percent free oil and 0.30 weight percent sodium sulfate with the balance being water. The viscosity of the sample at 75°F was 96.6 centipoises (cp), the viscosity data being the average of readings taken on a Brookfield viscometer at viscometer speeds of 6, 12, 30 and 60 RPM.

Once the viscosity of the alcohol sulfate had been determined, one weight percent, based on the weight of the slurry of a viscosity increasing additive was thoroughly admixed into the sample. Runs were again made on a Brookfield viscometer at 75°F, the viscosity data being the average of readings taken at viscometer speeds of 6, 12, 30 and 60 RPM. The results of such data are tabulated below:

| Additive | Viscosity at 75°F |
| --- | --- |
| None | 96.6 |
| triethylamine | 447.6 |
| tributylamine | 238.0 |
| 2-butoxyethanol | 488.3 |
| 2-hexoxyethanol | 996.5 |
| diethyleneglycol monohexyl ether | 548.5 |
| diethyl ether | 153.5 |
| dibutyl ether | 217.3 |
| dipentyl ether | 125.4 |
| dihexyl ether | 46.7 |

From the data shown above it is clear that by incorporating the viscosity increasing additive the viscosity of alcohol sulfate containing slurries can readily be increased. The data further indicates that when a tertiary amine is employed as the viscosity increasing additive, optimum results are obtained with the ethyl derivative. The data further shows that when alkoxyethoxyethanols are employed that the optimum results are obtained when the alkyl group is a hexyl. Likewise, the derivative of ethylene glycol produces better results than the derivative of diethylene glycol when the alkyl radical is identical. When the dialkyl ether is employed as the additive, the above data clearly indicates that dibutyl ether is preferred and further shows that when employing such dialkyl ether that if one employs an ether containing more than 5 carbon atoms in the alkyl groups that such dialkyl ether will act as viscosity reducing additives rather than the desired viscosity increasing additive.

Having thus described the invention, we claim:

1. An anionic surfactant slurry having an increased viscosity, said anionic slurry comprising from about 25 to about 60 weight percent anionic surfactant material; from about 0.5 to about 5 weight percent free oil; up to about 1 weight percent inorganic salt; up to about 75 weight percent water; and, as an essential ingredient, from about 0.2 to 6 weight percent of a viscosity increasing additive selected from the group consisting of alkoxyethoxyethanols having the general formula R''-O-$(CH_2CH_2O)_xH$, wherein $x$ varies from abbut 1 to 2 and R'' is an alkyl group containing from 2 to 6 carbon atoms.

2. The slurry of claim 1 wherein said anionic surfactant material is selected from the group consisting of: alcohol sulfates containing from about 10 to about 16 carbon atoms, ether sulfates containing from about 10 to about 16 carbon atoms and from about 0.5 to about 5.0 moles of ethylene oxide per mole of alcohol, alkylbenzene sulfonates containing from about 10 to about 14 carbon atoms in the alkyl portion, alkyl hydroxy sulfonates containing from about 12 to about 20 carbon atoms, alkene sulfonates containing from about 12 to about 20 carbon atoms, and mixtures thereof.

3. The slurry of claim 1 wherein the cationic portion of said sulfate and sulfonate material is selected from the group consisting of sodium, potassium, magnesium, ammonium and substituted amines.

4. The slurry of claim 1 wherein said viscosity increasing additive is an alkoxyethoxyethanol selected from the group consisting of 2-butoxyethanol, 2-hexoxy-ethanol, and diethylene glycol monohexyl ether.

5. The slurry of claim 4 wherein said alkoxyethoxyethanol is present in an amount of about 1 weight percent, said anionic surfactant material is a $C_{12}$-$C_{16}$ alcohol sulfate and is present in the range of about 30–35 weight percent, said free oil is present in an amount of from about 0.75 to 1.25 weight percent, said inorganic salt if Na2SO4 and is present in an amount up to about 0.5 weight percent with the balance being water.

6. A method for increasing the viscosity of anionic surfactant slurries, said method comprising admixing with said anionic surfactant slurries from about 0.2 to about 6 weight percent of a viscosity increasing additive selected from the group consisting of dialkyl ethers having the general formula R-O-R', wherein R and R' are alkyl groups containing from 2 to 5 carbon atoms, and alkoxyethoxyethanols having the general formula R''-O-($CH_2CH_2O$)$_x$H, wherein $x$ varies from about 1 to 2 and R'' is an alkyl group containing from 2 to 6 carbon atoms.

7. The method of claim 6 wherein said anionic surfactant is selected from compounds and mixtures of compounds selected from the group consisting of: alcohol sulfates containing from about 10 to about 16 carbon atoms, ether sulfates containing from about 10 to about 16 carbon atoms, and from about 0.5 to about 5.0 moles of ethylene oxide per mole of alcohol, alkylbenzene sulfonates containing from about 10 to about 14 carbon atoms in the alkyl portion, alkyl hydroxy sulfonates containing from about 12 to about 20 carbon atoms, alkene sulfonates containing from about 12 to about 20 carbon atoms, and mixtures thereof.

8. The method of claim 7 wherein said anionic slurry comprises from about 25 to about 60 weight percent anionic surfactant material, from about 0.5 to about 5.0 weight percent free oil, and up to about 1.0 weight percent inorganic salt with the balance being water, and wherein said cationic portion of said sulfate and sulfonate material is selected from the group consisting of sodium, potassium, magnesium, ammonium and substituted amines.

9. The method of claim 6 wherein said viscosity increasing additive is selected from the group consisting of diethyl ether, dibutyl ether, dipentyl ether and mixtures thereof.

10. The method of claim 9 wherein said dialkyl ether component is present in an amount of about 1 weight percent, said anionic surfactant material is a $C_{12}$-$C_{16}$ alcohol sulfate and is present in the range of about 30–35 weight percent, said free oil is present in an amount of from about 0.75 to 1.25 weight percent, said inorganic salt is $Na_2SO_4$ and is present in an amount up to about 0.5 weight percent with the balance being water.

11. The method of claim 6 wherein said viscosity increasing additive is an alkoxyethoxyethanol selected from the group consisting of 2-butoxyethanol, 2-hexoxyethanol, and diethylene glycol monohexyl ether.

12. The method of claim 11 wherein said alkoxyethoxyethanol is present in an amount of about 1 weight percent, said anionic surfactant material is a $C_{12}$-$C_{16}$ alcohol sulfate and is present in the range of about 30–35 weight percent, said free oil is present in an amount of from about 0.75 to 1.25 weight percent, said inorganic salt is $Na_2SO_4$ and is present in an amount up to about 0.5 weight percent with the balance being water.

* * * * *